(12) United States Patent
Sugie et al.

(10) Patent No.: US 10,492,661 B2
(45) Date of Patent: Dec. 3, 2019

(54) CONTROL DEVICE, MEDICAL DEVICE, AND MEDICAL DEVICE SYSTEM

(71) Applicant: SONY CORPORATION, Tokyo (JP)

(72) Inventors: Yuki Sugie, Kanagawa (JP); Tomoyuki Hirayama, Kanagawa (JP); Yasuaki Takahashi, Kanagawa (JP); Masahito Yamane, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/283,003

(22) Filed: Feb. 22, 2019

(65) Prior Publication Data
US 2019/0183317 A1 Jun. 20, 2019

Related U.S. Application Data

(63) Continuation of application No. 15/563,812, filed as application No. PCT/JP2016/063618 on May 6, 2016, now Pat. No. 10,251,531.

(30) Foreign Application Priority Data

May 19, 2015 (JP) .................................. 2015-101735

(51) Int. Cl.
*G08B 13/00* (2006.01)
*A61B 1/00* (2006.01)
*G02B 23/24* (2006.01)

(52) U.S. Cl.
CPC ...... *A61B 1/00055* (2013.01); *A61B 1/00006* (2013.01); *A61B 1/00016* (2013.01);
(Continued)

(58) Field of Classification Search
CPC ............ A61B 1/00055; A61B 1/00016; A61B 1/00006; A61B 1/00062; G08B 23/00; G02B 23/24; H04Q 5/22
(Continued)

(56) References Cited

U.S. PATENT DOCUMENTS 8,554,033 B2 10/2013 Kewitsch
8,749,396 B2 6/2014 Maggiore
(Continued)

FOREIGN PATENT DOCUMENTS

JP 5-317249 A 12/1993
JP 2001-95763 A 4/2001
(Continued)

OTHER PUBLICATIONS

English translation of the International Search Report and Written Opinion dated Jul. 19, 2016 in PCT/JP2016/063618.

*Primary Examiner* — Toan N Pham
(74) *Attorney, Agent, or Firm* — Xsensus, LLP (57) ABSTRACT

The present disclosure relates to a control device, a medical device, and a medical device system that enable to provide a user who tries to connect the medical device to the control device with user support information including a result of compatibility determination between the devices.

A control device according to one aspect of the present disclosure is provided with a connector joint to which a connector unit provided on a cable extending from a medical device is connected, a communication unit that performs radio communication with the connector unit by proximity radio communication, and a notification unit that notifies a user of user support information based on information from the medical device received by the communication unit. The present disclosure is applicable to an endoscopic surgical system, for example.

16 Claims, 7 Drawing Sheets

(52) U.S. Cl.
CPC ...... *A61B 1/00059* (2013.01); *A61B 1/00062* (2013.01); *A61B 1/00114* (2013.01); *A61B 1/00124* (2013.01); *G02B 23/24* (2013.01); *G02B 23/2476* (2013.01)

(58) Field of Classification Search
USPC ............ 340/505, 568.1, 686.6, 687; 600/117
See application file for complete search history.

(56) References Cited

U.S. PATENT DOCUMENTS

| | | |
|---|---|---|
| 9,510,740 B2 * | 12/2016 | Hopkins ............ A61B 1/00016 |
| 2011/0012727 A1 | 1/2011 | Pance et al. |
| 2011/0037876 A1 | 2/2011 | Talbert et al. |
| 2011/0193948 A1 | 8/2011 | Amling |

FOREIGN PATENT DOCUMENTS

| | | |
|---|---|---|
| JP | 2006-255192 A | 9/2006 |
| JP | 2011-135984 A | 7/2011 |
| JP | 2012-533789 A | 12/2012 |
| JP | 2013-502185 A | 1/2013 |

\* cited by examiner

CONTROL DEVICE, MEDICAL DEVICE, AND MEDICAL DEVICE SYSTEM

TECHNICAL FIELD

The present disclosure relates to a control device, a medical device, and a medical device system, and especially relates to a control device, a medical device, and a medical device system capable of determining compatibility between the control device and the medical device which may be connected to the control device via a cable.

BACKGROUND ART

In recent years, an endoscopic surgical procedure using an endoscope is performed in a medical field instead of a laparotomy conventionally adopted. An endoscopic surgical system is arranged in an operating room where the endoscopic surgical procedure is performed.

The endoscopic surgical system includes the endoscope, a camera control unit (CCU) that controls the endoscope, an energy treatment tool, and a device for treatment tool that supplies high-frequency current thereto.

In the endoscopic surgical system described above, a connector provided at the end of a cable extending from the endoscope is inserted into an input interface (connector insertion port) of the CCU, so that both are connected to each other. That is, if shapes of the connector insertion port and the connector are roughly matched, various types of endoscopes may be physically connected to the CCU.

However, even if a certain endoscope may be physically connected to the CCU, in a case where the CCU and the endoscope are not compatible with each other, there might be a problem that an imaged image is not displayed, the image is displayed but with disturbance, or an unintended image is displayed. Furthermore, at least one of the CCU and the endoscope might be electrically damaged, or at least one of the connector insertion port of the CCU and the connector of the endoscope might be physically damaged.

Therefore, as a method of coping with the above-mentioned problem, there conventionally is proposed a method of providing indices representing compatible standards and their version numbers with colors in the vicinity of the connector insertion port of the CCU and on the connector of the endoscope (refer to, for example, Patent Document 1).

According to the method disclosed in Patent Document 1, a user may compare the color of the index provided on the CCU with the color of the index provided on the connector of the endoscope to determine whether the both are compatible with each other.

CITATION LIST

Patent Document

Patent Document 1: Japanese Patent Application Laid-Open No. 5-317249

SUMMARY OF THE INVENTION

Problems to be Solved by the Invention

However, the method of Patent Document 1 merely provides a determination criterion to the user, and the user should finally determine. Therefore, it is desirable that a mechanism capable of determining whether the CCU and the endoscope connected thereto are compatible with each other appears.

Meanwhile, such a problem that connectability should be determined is also present not only in a combination of the CCU and the endoscope but also in a combination of other devices connected via a cable such as a combination of a device for treatment tool 7 and an energy treatment tool 3, so that it is expected that they may also be solved by a similar method.

Hereinafter, out of the two devices connected via the cable having the above-mentioned problem, a device (CCU and the like) on a side on which the connector insertion port is provided is referred to as a control device, and a device (endoscope and the like) on a side connected to the control device via the cable is referred to as a medical device.

The present disclosure has been achieved in view of such a situation, and an object thereof is to provide a user who tries to connect the medical device to the control device with user support information including a result of a compatibility determination between the devices.

Solutions to Problems

A control device according to a first aspect of the present disclosure is provided with a connector joint to which a connector unit provided on a cable extending from a medical device is connected, a communication unit that performs radio communication with the connector unit by proximity radio communication, and a notification unit that notifies a user of user support information based on information from the medical device received by the communication unit.

The notification unit may notify the user whether the control device and the medical device are officially compatible with each other as the user support information.

The control device according to the first aspect of the present disclosure may be further provided with a compatibility determination unit that determines whether the control device and the medical device are officially compatible with each other on the basis of attribute information of the medical device received by the communication unit, in which the notification unit may notify the user of a determination result of the compatibility determination unit as the user support information.

A determination criterion when the compatibility determination unit determines whether the control device and the medical device are officially compatible with each other on the basis of the attribute information of the medical device is able to be updated.

The control device according to the first aspect of the present disclosure may further be provided with a connection determination unit that determines whether electrical connection between the control device and the medical device is stable, in which the notification unit may further notify the user of a determination result of the connection determination unit as the user support information in a state where the connector unit is connected to the connector joint.

The notification unit may notify the user whether an orientation of the connector unit matches the connector joint as the user support information in a state where the connector unit is not connected to the connector joint.

The notification unit may notify whether the medical device is already subjected to sterilization treatment as the user support information on the basis of the information from the medical device received by the communication unit.

The notification unit may notify of information regarding the number of times of use or using time of the medical device as the user support information on the basis of the information from the medical device received by the communication unit.

In the first aspect of the present disclosure, the radio communication is performed with the connector unit of the medical device by proximity radio communication and the user is notified of the user support information based on the information received from the medical device.

A medical device according to a second aspect of the present disclosure is provided with a connector unit for connecting to a control device via a cable, a communication unit that performs radio communication with the control device by proximity radio communication, and a notification unit that notifies a user of user support information based on information from the control device received by the communication unit.

The notification unit may notify the user whether the control device and the medical device are officially compatible with each other as the user support information.

The communication unit may transmit attribute information of the medical device to the control device and receive compatibility information indicating whether the control device and the medical device are officially compatible with each other transmitted from the control device, and the notification unit may notify the user whether the control device and the medical device are officially compatible with each other as the user support information on the basis of the received compatibility information.

The medical device according to the second aspect of the present disclosure may further be provided with a compatibility determination unit that determines whether the control device and the medical device are officially compatible with each other on the basis of attribute information of the control device received by the communication unit, in which the notification unit notifies the user of a determination result of the compatibility determination unit as the user support information.

A determination criterion when the compatibility determination unit determines whether the control device and the medical device are officially compatible with each other on the basis of the attribute information of the control device is able to be updated.

The notification unit may further notify the user whether electrical connection between the control device and the medical device is stable as the user support information in a state where the connector unit is connected to the control device.

The notification unit may notify the user whether an orientation of the connector unit matches a connector joint of the control device as the user support information in a state where the connector unit is not connected to the control device.

The notification unit may notify the user whether sterilization treatment of the medical device is already performed as the user support information.

The notification unit may notify the user of information regarding the number of times of use or using time of the medical device as the user support information.

In the second aspect of the present disclosure, the radio communication is performed with the control device by proximity radio communication and the user is notified of the user support information based on the information from the control device.

A medical device system according to a third aspect of the present disclosure is a medical device system provided with a control device and a medical device connected to the control device via a cable, in which the control device is provided with a connector joint connected to a connector unit of the medical device, a first communication unit that performs radio communication with the connector unit of the medical device by proximity radio communication, and a first notification unit that notifies a user of user support information based on information from the medical device received by the communication unit, and the connector unit of the medical device is provided with a second communication unit that performs radio communication with the first communication unit of the control device by proximity radio communication, and a second notification unit that notifies the user of the user support information based on information from the control device received by the second communication unit.

In the third aspect of the present disclosure, the radio communication is performed between the control device and the connector unit of the medical device by proximity radio communication and the user is notified of the user support information based on the information from the medical device.

Effects of the Invention

According to the first to third aspects of the present disclosure, it is possible to provide the user support information including the result of the compatibility determination between the devices to the user who tries to connect the medical device to the control device.

MODE FOR CARRYING OUT THE INVENTION

A best mode for carrying out the present disclosure (hereinafter, referred to as an embodiment) is hereinafter described in detail with reference to the drawings.

<Configuration Example of Endoscopic Surgical System Including Medical Device System to which Present Disclosure is Applied>

First, a configuration example of an endoscopic surgical system including a medical device system to which the present disclosure is applied is described.

Figure 1:
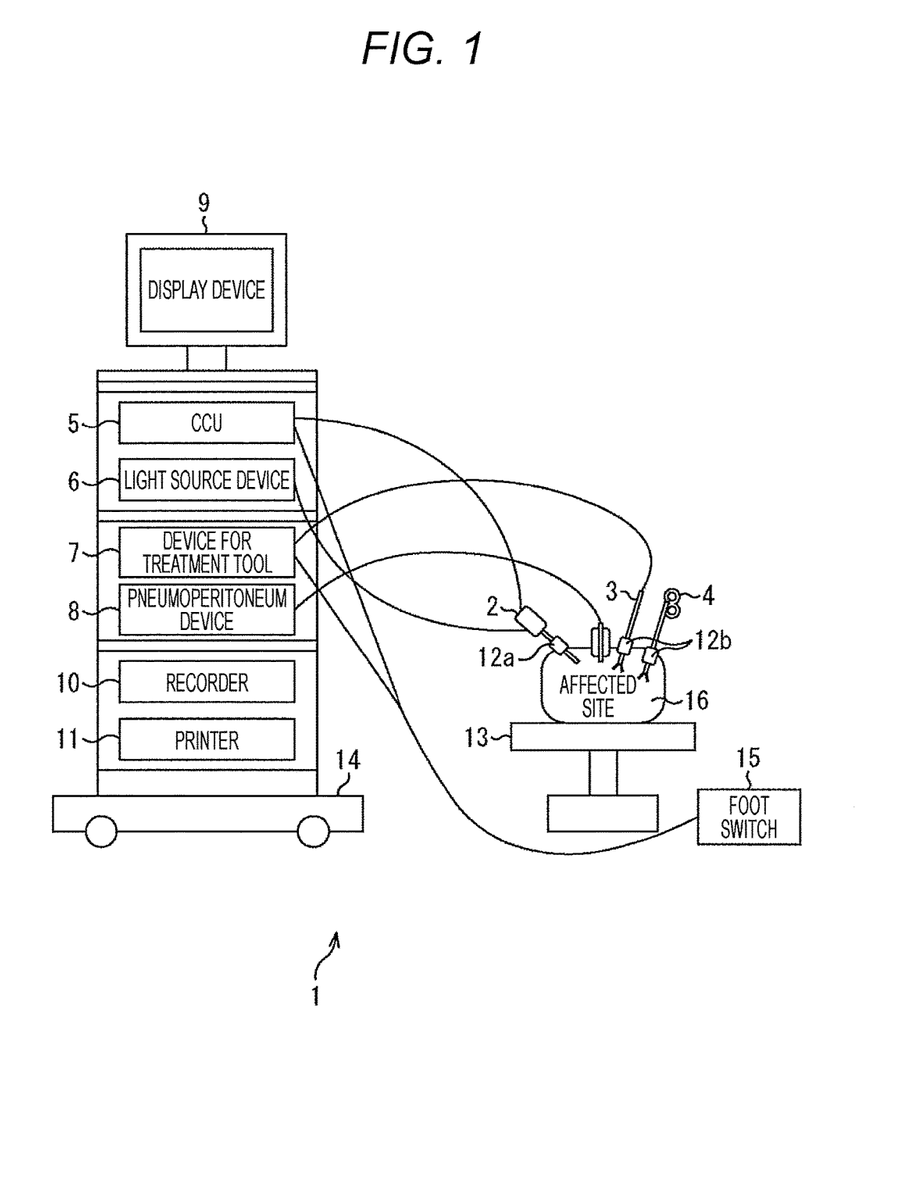
FIG. 1 is a block diagram illustrating a configuration example of an endoscopic surgical system.

FIG. 1 illustrates the configuration example of the endoscopic surgical system arranged in an operating room where an endoscopic surgical procedure is performed.

An endoscopic surgical system 1 includes an endoscope (also referred to as a laparoscope) 2 and an energy treatment tool 3 to be inserted into a body of a patient, and a camera control (CCU) 5, a light source device 6, a device for treatment tool 7 and the like to which they are connected by cables. A foot switch 15 is further connected to the CCU 5 and the device for treatment tool 7. The endoscopic surgical system 1 also includes a pneumoperitoneum device 8, a display device 9, a recorder 10, and a printer 11. The units from the CCU 5 to the printer 11 are mounted on a movable cart 14.

The endoscope 2 outputs a moving image signal of an affected site 16 imaged by means of an observation optical system to the CCU 5 via a video cable. Also, the endoscope 2 is connected to the light source device 6 via a light guide cable. As a result, the endoscope 2 may irradiate the affected site 16 by switching light of various wavelengths.

The energy treatment tool 3 connected to the device for treatment tool 7 via an electric cable is used when resecting the affected site 16 by electric heat, for example, by high-frequency current supplied from the device for treatment tool 7.

The CCU 5 performs predetermined signal processing on the moving image signal from the endoscope 2, outputs a result thereof to the display device 9, and displays an endoscopic image (moving image) of the affected site 16.

The light source device 6 supplies light to the endoscope 2 via the light guide cable. Meanwhile, there also is a case where the light source device 6 supplies power for power supply via the cable and a light source is provided on a side of the endoscope 2. The device for treatment tool 7 supplies the high-frequency current to the energy treatment tool 3 via the electric cable. The pneumoperitoneum device 8 having an air supplying/sucking function may supply air to, for example, the abdominal region in the body of the patient.

The display device 9 displays the moving image of the affected site 16 imaged by the endoscope 2. The recorder 10 records the moving image and the like of the affected site 16 imaged by the endoscope 2. The printer 11 prints the image and the like of the affected site 16 imaged by the endoscope 2.

The foot switch 15 outputs a trigger signal corresponding to a foot operation by an operator, an assistant and the like to the CCU 5, the device for treatment tool 7 and the like. As a result, the operator, assistant and the like may control the CCU 5, the device for treatment tool 7 and the like with the toes.

In the endoscopic surgical procedure using the endoscopic surgical system 1, instead of incising the abdominal wall and opening the abdomen, opening tools referred to as trocars 12a and 12b are attached to several positions of the abdominal wall and the endoscope 2, the energy treatment tool 3, forceps 4 and the like are inserted into the body from the trocars 12a and 12b. Then, treatment such as resection of the affected site 16 with the energy treatment tool 3 and the like is performed while the moving image of the affected site (tumor and the like) 16 imaged by the endoscope 2 is watched in real time. Meanwhile, the endoscope 2, the energy treatment tool 3, the forceps 4 and the like are held by the operator, the assistant, a scopist, a robot and the like.

Meanwhile, in the endoscopic surgical system 1 illustrated in FIG. 1, a combination of the endoscope 2 and the CCU 5, a combination of the endoscope 2 and the light source device 6, a combination of the energy treatment tool 3 and the device for treatment tool 7 and the like correspond to a combination of the medical device and a control device in the present disclosure. Also, although not illustrated, a surgical microscope, the CCU corresponding thereto and the like in a microscopic surgical system are also similar to them.

<Configuration Example of Medical Device System to which Present Disclosure is Applied>

Figure 2:
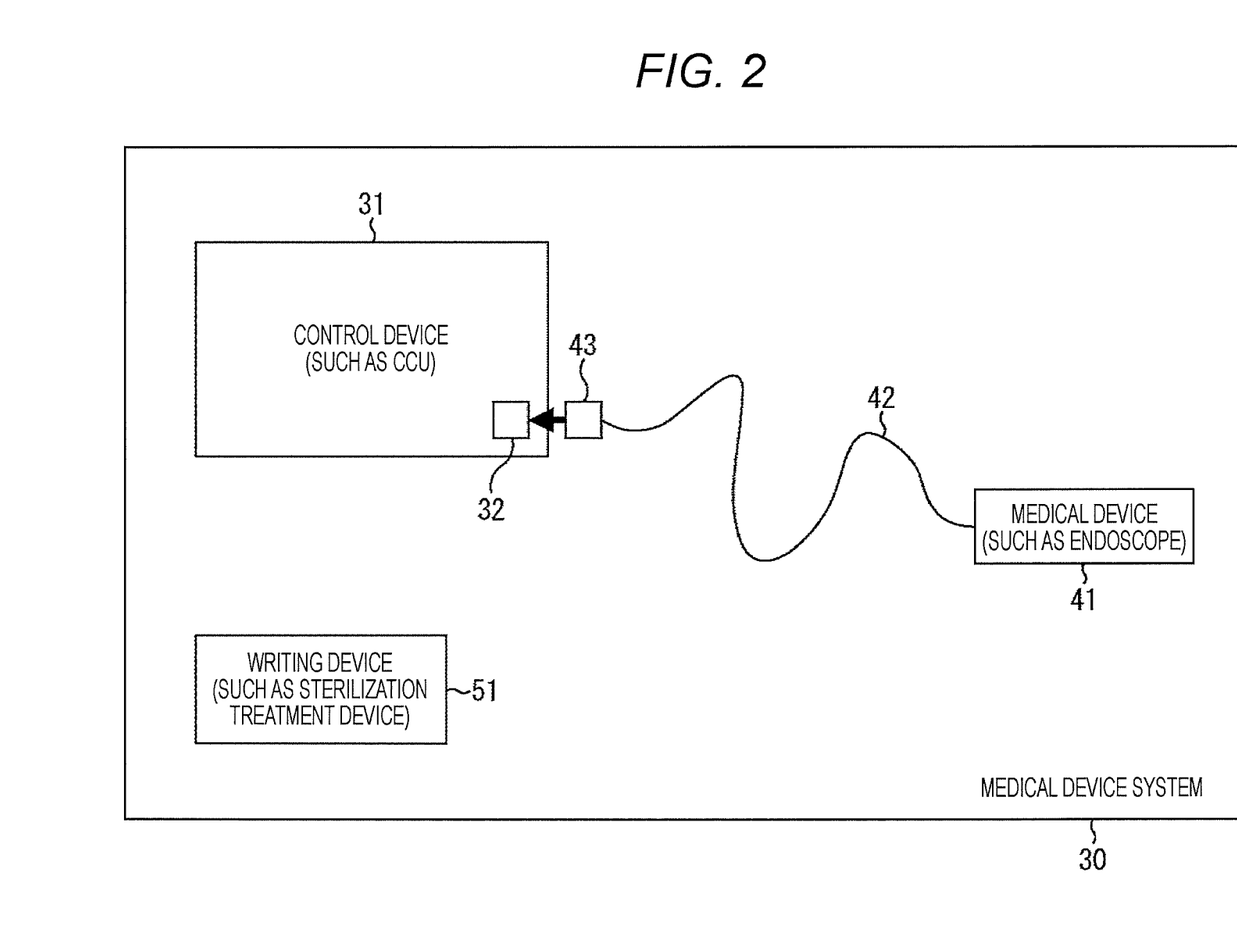
FIG. 2 is a block diagram illustrating a configuration example of a medical device system to which the present disclosure is applied.

FIG. 2 illustrates a configuration example of the medical device system to which the present disclosure is applied. A medical device system 30 is formed of a control device 31, a medical device 41, and a writing device 51.

The control device 31 corresponding to the CCU 5 and the like in the above-described endoscopic surgical system 1, for example, includes a connector joint (connector insertion port) 32. The control device 31 controls the medical device 41 connected thereto and processes signals transmitted from the medical device 41.

The medical device 41 corresponding to the endoscope 2 in the above-described endoscopic surgical system 1, for example, is connected to the control device 31 via a cable 42. Specifically, when the user inserts a connector unit 43 provided at the end of the cable 42 extending from the medical device 41 into the connector joint 32 of the control device 31, the control device 31 and the medical device 41 are physically and electrically connected to each other.

The writing device 51 corresponds to a sterilization treatment device and the like (not illustrated) arranged in the operating room together with the above-described endoscopic surgical system 1 to perform sterilization treatment on a used medical device 41. The writing device 51 may write predetermined information (for example, information indicating whether the sterilization treatment is already performed and the like) in a storage unit 73 (FIG. 4) of the medical device 41.

Figure 3:
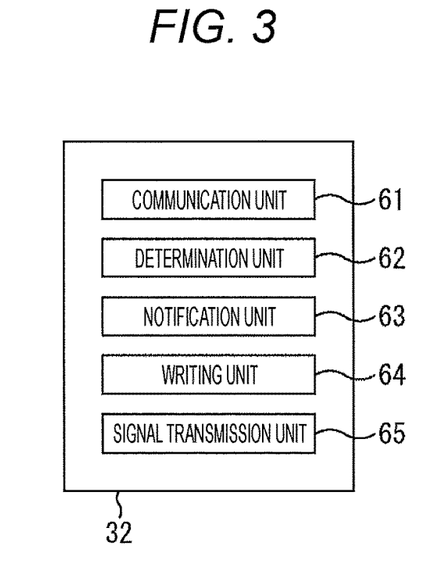
FIG. 3 is a block diagram illustrating a configuration example of a connector joint provided on a control device.

Next, FIG. 3 illustrates a configuration example of the connector joint 32 provided on the control device 31. The connector joint 32 includes a communication unit 61, a determination unit 62, a notification unit 63, a writing unit 64, and a signal transmission unit 65.

In a case where the connector unit 43 of the medical device 41 is brought closer to the connector joint 32 by near field communication (NFC) (short-range radio communication technology) represented by FeliCa (trademark), the communication unit 61 performs radio communication with a communication unit 71 of the connector unit 43 (FIG. 4) and obtains attribute information of the medical device 41 and orientation information of the connector unit 43 from the connector unit 43 to output to the determination unit 62. Also, the communication unit 61 transmits results of compatibility determination, electrical connection determination, and orientation determination by the determination unit 62 to the communication unit 71. Meanwhile, the communication between the communication unit 61 and the communication unit 71 may adopt a short-range radio communication technology other than NFC.

On the basis of attribute information of the control device 31 which is held and the attribute information of the medical device 41 input from the communication unit 61, the determination unit 62 determines whether the control device 31 and the medical device 41 are officially compatible with each other (compatibility determination) and outputs the result of the compatibility determination to the communication unit 61 and the notification unit 63.

Herein, "officially compatible" in this specification is intended to mean a relationship in which the manufacturer, distributor, official import agent and the like of at least one of the control device 31 and the medical device 41 confirm that the control device 31 and the medical device 41 are physically connectable to each other without trouble, and that the control device 31 and the medical device 41 normally operate in a case where they are connected to each other. However, the "normal operation" also includes a state where backward compatibility is maintained, a state in which a part of functions of the control device 31 or the medical device 41 is restricted and the like depending on a software version of the control device 31 and the medical device 41.

Meanwhile, for example, as the compatibility determination by the determination unit 62, it is also possible to allow the determination unit 62 to hold a look-up table (LUT) in advance. In this case, it is desirable that the LUT may be always automatically updated to the latest one. Alternatively, the compatibility determination may also be executed by a unit other than the determination unit 62. For example, this may be executed by the medical device 41 side or may be executed on a predetermined server.

Also, after the connector unit 43 is inserted into the connector joint 32, the determination unit 62 determines whether the electrical connection therebetween is stable (electrical connection determination) and outputs the result of the electrical connection determination to the notification unit 63.

Furthermore, the determination unit 62 determines whether the orientation in a case of connecting the connector joint 32 is correct (orientation determination) on the basis of the orientation information of the connector unit 43 and outputs the result of the orientation determination to the notification unit 63.

The notification unit 63 includes a mechanism for notifying the user of the results of the compatibility determination, the electric connection determination, and the orientation determination by the determination unit 62. Specifically, this includes any one of a light emitter that flashes and lights in plural colors, an alarm that generates a warning sound and the like, a vibrator that vibrates, a display that displays character strings, icons, pictures and the like, an output interface that outputs character string, icons, pictures and the like to an external monitor and the like.

The writing unit 64 writes predetermined information in the storage unit 73 of the medical device 41 via the communication unit 61. The signal transmission unit 65 communicates signals (control signal, video signal and the like) between the control device 31 and the medical device 41 after the connection is established therebetween.

Figure 4:
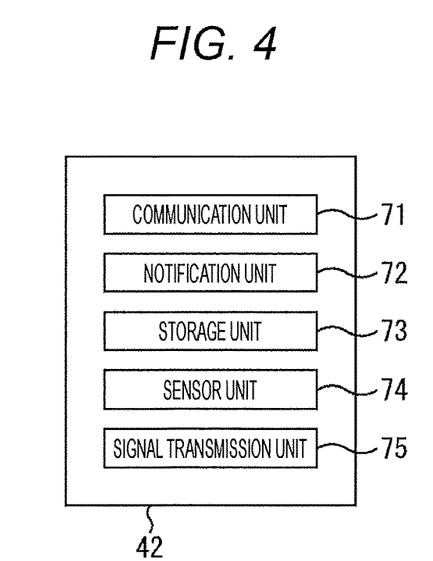
FIG. 4 is a block diagram illustrating a configuration example of a connector unit of the medical device.

Next, FIG. 4 illustrates a configuration example of the connector unit 43 provided at the end of the cable 42 extending from the medical device 41. The connector unit 43 includes the communication unit 71, a notification unit 72, the storage unit 73, a sensor unit 74, and a signal transmission unit 75.

In a case where the connector unit 43 is brought closer to the connector joint 32 of the control device 31, the communication unit 71 performs the radio communication with the communication unit 61 of the connector joint 32 by NFC and transmits the attribute information of the medical device 41 and the orientation information indicating the orientation of the connector unit 43 stored in the storage unit 73 to the communication unit 61. Also, the communication unit 71 supplies the results of the compatibility determination, the electrical connection determination, and the orientation determination transmitted from the connector joint 32 to the notification unit 72. Meanwhile, by using NFC, the communication unit 71 may obtain driving power thereof by electromagnetic induction based on an electromagnetic wave transmitted from the communication unit 61. The communication unit 71 may also be driven using power supply on the medical device 41 side.

The notification unit 72 includes a mechanism for notifying the user of the results of the compatibility determination, the electrical connection determination, and the orientation determination. Specifically, this includes a light emitter that flashes and lights in plural colors and the like.

The storage unit 73 stores the attribute information of the medical device 41. The storage unit 73 also stores predetermined information transmitted from the connector joint 32 or the writing device 51 via the communication unit 71.

The sensor unit 74 detects the orientation of the connector unit 43 and notifies the communication unit 71 of the orientation information indicating a detection result.

The signal transmission unit 75 communicates signals (control signal, video signal and the like) between the control device 31 and the medical device 41 after the connection is established therebetween.

Figure 5:
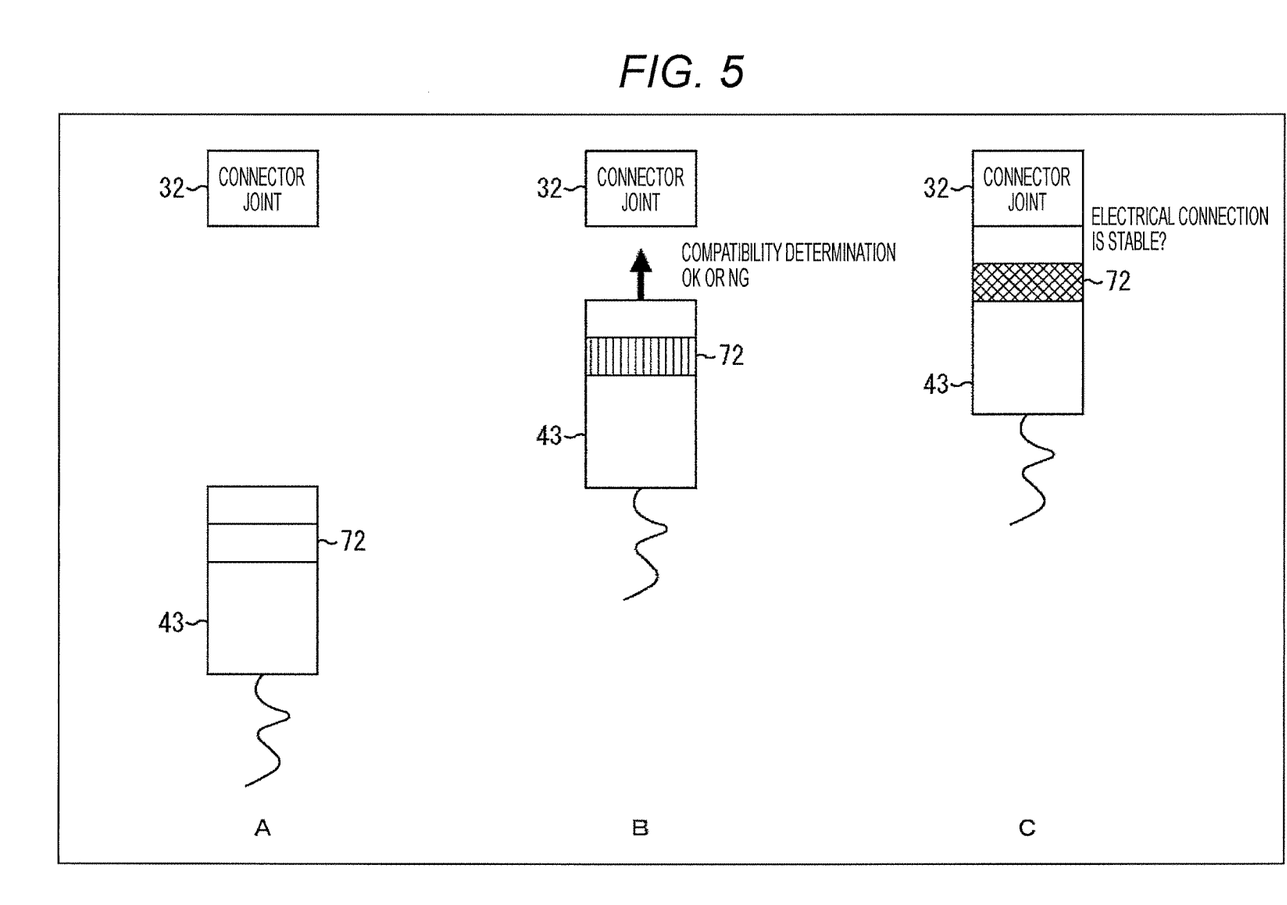
FIG. 5 is a view illustrating an example of notifying a user of compatibility.

Next, FIG. 5 illustrates an example of a method of notifying the user of the results of the compatibility determination, the electrical connection determination, and the orientation determination by the notification unit 72 of the connector unit 43.

As illustrated in A of FIG. 5, in a case where the connector unit 43 does not approach a range at a predetermined distance from the connector joint 32, the light emitter of the notification unit 72 is turned off. Thereafter, when the connector unit 43 approaches the range at a predetermined distance from the connector joint 32, the compatibility determination is performed, and as illustrated in B of FIG. 5, there is notification of the result of the compatibility determination by a color and a state of flashing and lighting of the light emitter of the notification unit 72. Furthermore, when the connector unit 43 is inserted into the connector joint 32, the electrical connection determination is performed, and as illustrated in C of FIG. 5, there is notification of the result of the electrical connection determination by the color and the state of flashing and lighting of the light emitter of the notification unit 72. Meanwhile, a specific example of the color and the state of flashing and lighting of the light emitter of the notification unit 72 is described later.

Figure 6:
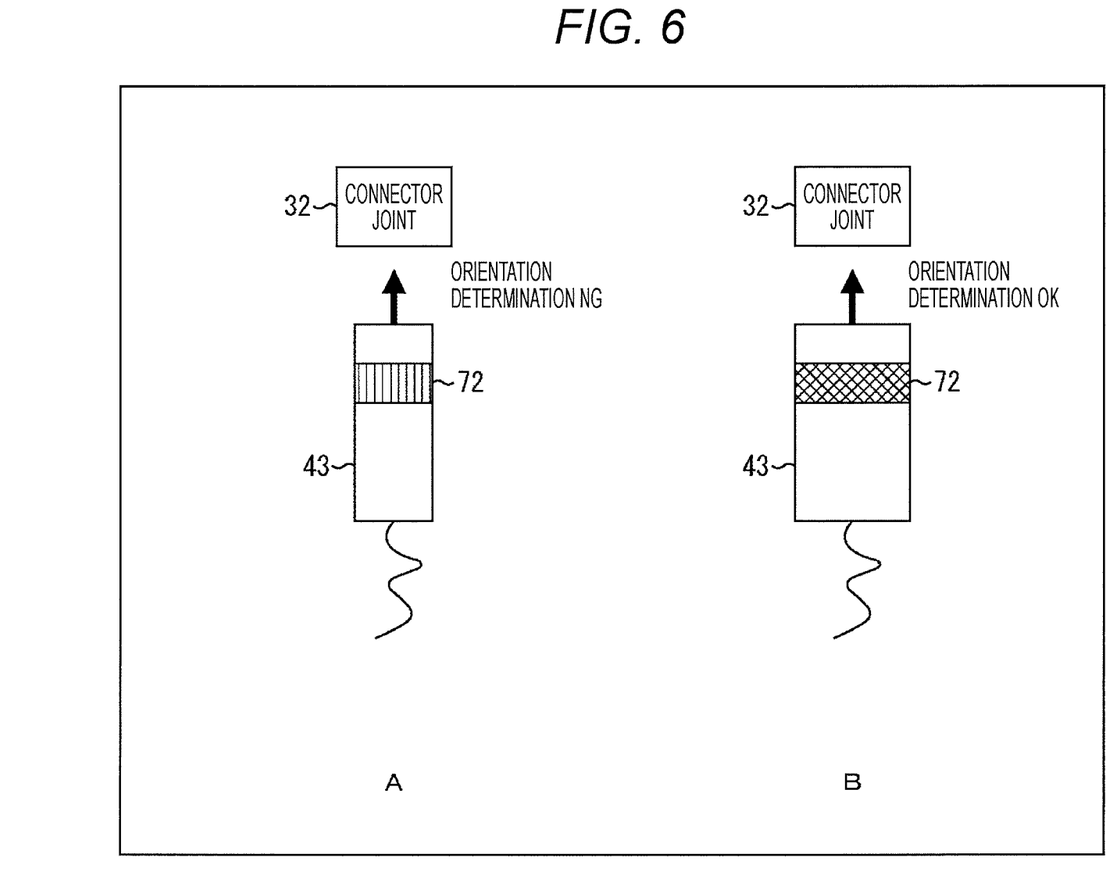
FIG. 6 is a view illustrating an example of notifying the user of the compatibility.

FIG. 6 illustrates an example of a method of notifying the user of the result of the orientation determination by the notification unit 72 of the connector unit 43.

In a case where the connector unit 43 does not approach the range at a predetermined distance from the connector joint 32, the notification unit is turned off. Thereafter, when the connector unit 43 approaches the range at a predetermined distance from the connector joint 32, the orientation determination is performed. The color and the state of flashing and lighting of the notification unit 72 are different between a case where the result of the orientation determination is NG (B of FIG. 6) and a case where the result of the orientation determination is OK (C of FIG. 6). Meanwhile, it is also possible that execution of the orientation determination and notification thereof are performed only in a case where the result of the compatibility determination is OK.

<Connectability Notifying Process of Medical Device System 30>

Figure 7:
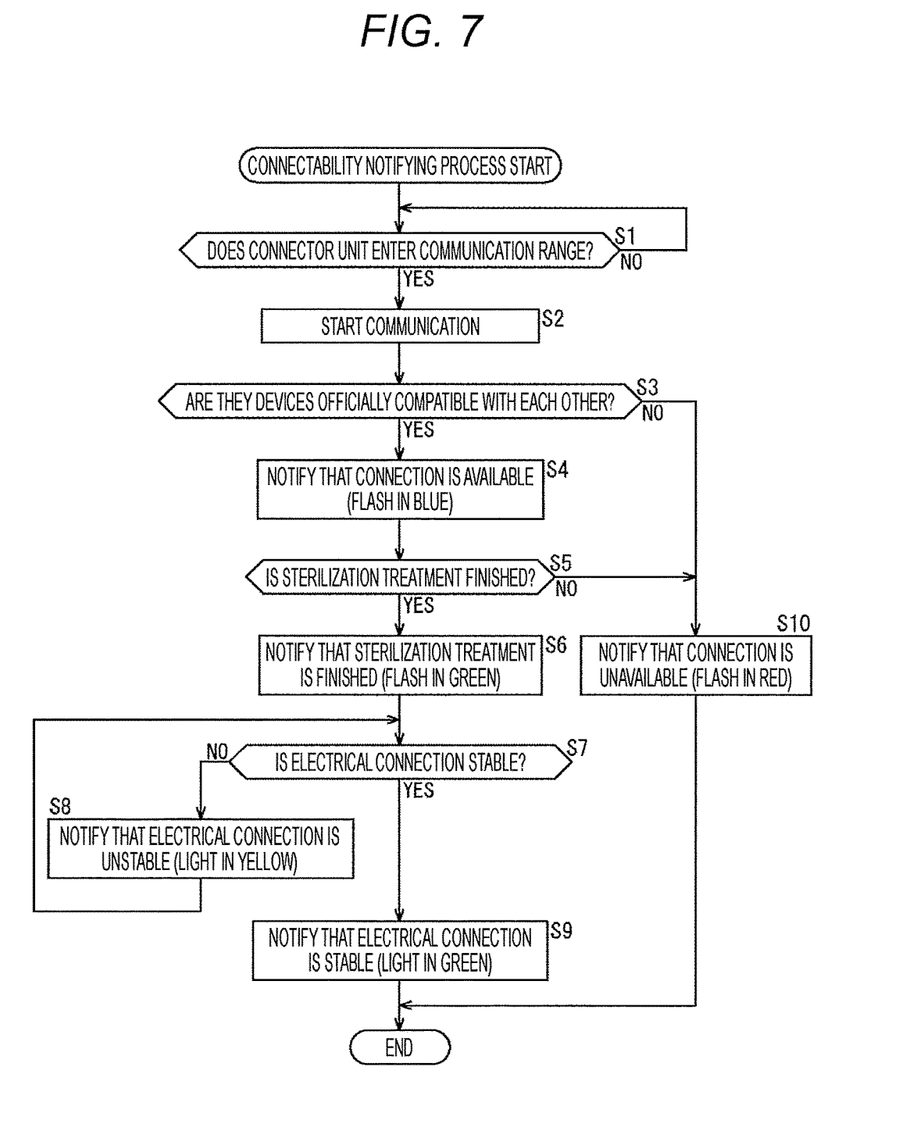
FIG. 7 is a flowchart illustrating a connection determining process.

Next, FIG. 7 is a flowchart illustrating a connectability notifying process by the medical device system 30.

At step S1, the communication unit 61 of the connector joint 32 stands by until a counterpart with which the radio communication may be performed by NFC (in this case, the communication unit 71 of the connector unit 43) enters a communication range. In a case where the counterpart with which the radio communication may be performed enters the communication range, the procedure shifts to step S2.

At step S2, the communication unit 61 starts the radio communication with the communication unit 71 of the connector unit 43 and obtains the attribute information of the medical device 41, the orientation information of the connector unit 43, and the information indicating whether the sterilization treatment is already performed stored in the storage unit 73 of the connector unit 43 to output to the determination unit 62.

At step S3, the determination unit 62 performs the compatibility determination on the basis of the attribute information of the control device 31 which is held and the attribute information of the medical device 41 input from the communication unit 61 and outputs the result thereof to the communication unit 61 and the notification unit 63. The communication unit 61 transmits the result of the compatibility determination by the determination unit 62 to the communication unit 71.

In a case where it is determined to be compatible in the compatibility determination at step S3 (the control device 31 and the medical device 41 are officially compatible with each other), the procedure shifts to step S4.

At step S4, the notification unit 63 of the connector joint 32 and the notification unit 72 of the connector unit 43 notify the user that it is possible connect. Specifically, for example, a built-in light emitter flashes in blue.

Next, at step S5, on the basis of the information indicating whether the medical device 41 is already subjected to the sterilization treatment input from the communication unit 61, the determination unit 62 determines whether the medical device 41 is already subjected to the sterilization treatment and notifies the notification unit 63 of the determination result. In a case where the sterilization treatment is already performed, the procedure shifts to step S6.

At step S6, the notification unit 63 of the connector joint 32 notifies the user that the sterilization treatment is already performed. Specifically, for example, the light emitter currently flashing in blue is changed to flash in green. At that time, the notification unit 72 of the connector unit 43 may similarly change the light emitter flashing in blue to flash in green.

When the user who confirms flashing in green inserts the connector unit 43 into the connector joint 32, the determination unit 62 performs the electrical connection determination between the connector unit 43 and the connector joint 32 at step S7 and outputs the result thereof to the communication unit 61 and the notification unit 63. The communication unit 61 transmits the result of the electrical connection by the determination unit 62 to the communication unit 71.

In a case where the result of the electrical connection determination at step S7 is negative (the electrical connection between the connector unit 43 and the connector joint 32 is unstable), the procedure shifts to step S8.

At step S8, the notification unit 63 of the connector joint 32 and the notification unit 72 of the connector unit 43 notify the user that the electrical connection is unstable. Specifically, for example, the light emitter currently flashing in green is changed to flash in yellow. Thereafter, the procedure returns to step S7.

In a case where the user who confirms flashing in yellow inserts the connector unit 43 into the connector joint 32 again and the result of the electrical connection determination at step S7 is positive (electrical connection between the connector unit 43 and the connector joint 32 is stable), the procedure shifts to step S9.

At step S9, the notification unit 63 of the connector joint 32 and the notification unit 72 of the connector unit 43 notify the user that the electrical connection is stable. Specifically, for example, the light emitter currently flashing in green is changed to light in green. Thereafter, signals (control signal, video signal and the like) are communicated between the signal transmission unit 65 of the connector joint 32 and the signal transmission unit 75 of the connector unit 43. Also, the writing unit 64 writes information indicating that the medical device 41 is already used after the sterilization treatment (this means that the device is not sterilized) in the storage unit 73 of the connector unit 43 via the communication unit 61.

Meanwhile, in a case where it is determined that it is not compatible in the compatibility determination at step S3 (the control device 31 and the medical device 41 are not officially compatible with each other), the procedure shifts to step S10. Additionally, in a case where it is determined that the sterilization treatment is not already performed in the determination at step S5 also, the procedure shifts to step S10.

At step S10, the notification unit 63 of the connector joint 32 and the notification unit 72 of the connector unit 43 notify the user that it is not possible to connect. Specifically, for example, the built-in light emitter flashes in red. The connectability notifying process is finished.

Meanwhile, the process at each step S of the connectability notifying process may be performed in time series as described above or may be performed in parallel.

According to the connectability notifying process, in a case where the notification units 63 and 72 flash in green after flashing in blue (in a case where they are devices officially compatible with each other and the sterilization treatment is already performed), the user may insert the connector unit 43 into the connector joint 32. Thereafter, if the notification units 63 and 72 light in green, they may be directly used normally.

After the connector unit 43 is inserted into the connector joint 32, in a case where the notification units 63 and 72 flash in yellow (in a case where electrical connection is unstable), it is possible to insert the connector unit 43 into the connector joint 32 again. Thereafter, if the notification units 63 and 72 light in green, they may be directly used normally.

In a case where the notification units 63 and 72 flash in red without flashing in blue (in a case where they are not officially compatible with each other), the user cannot connect the medical device 41 to the control device 31.

In a case where the notification units 63 and 72 flash in red after flashing in blue (in a case where the devices are officially compatible with each other but not sterilized), the user should perform the sterilization treatment on the medical device 41 by the sterilization treatment device (writing device 51). In this case, when the sterilization treatment is finished, information indicating that the sterilization treatment is completed is written in the storage unit 73 of the connector unit 43 by the sterilization treatment device (writing device 51).

As described above, according to the medical device system 30, there may be notification of user support information indicating whether the medical device 41 is officially compatible with the control device 31, whether the medical device 41 is subjected to the sterilization treatment, whether the electrical connection is stable (whether the connector unit 43 is not half-inserted), and whether the orientation of the connector 43 with respect to the connector joint 32 is correct. As a result, it is possible to prevent the user from causing a mistake or accident in the medical field.

<Another Configuration Example of Medical Device System to which Present Disclosure is Applied>

Figure 8:
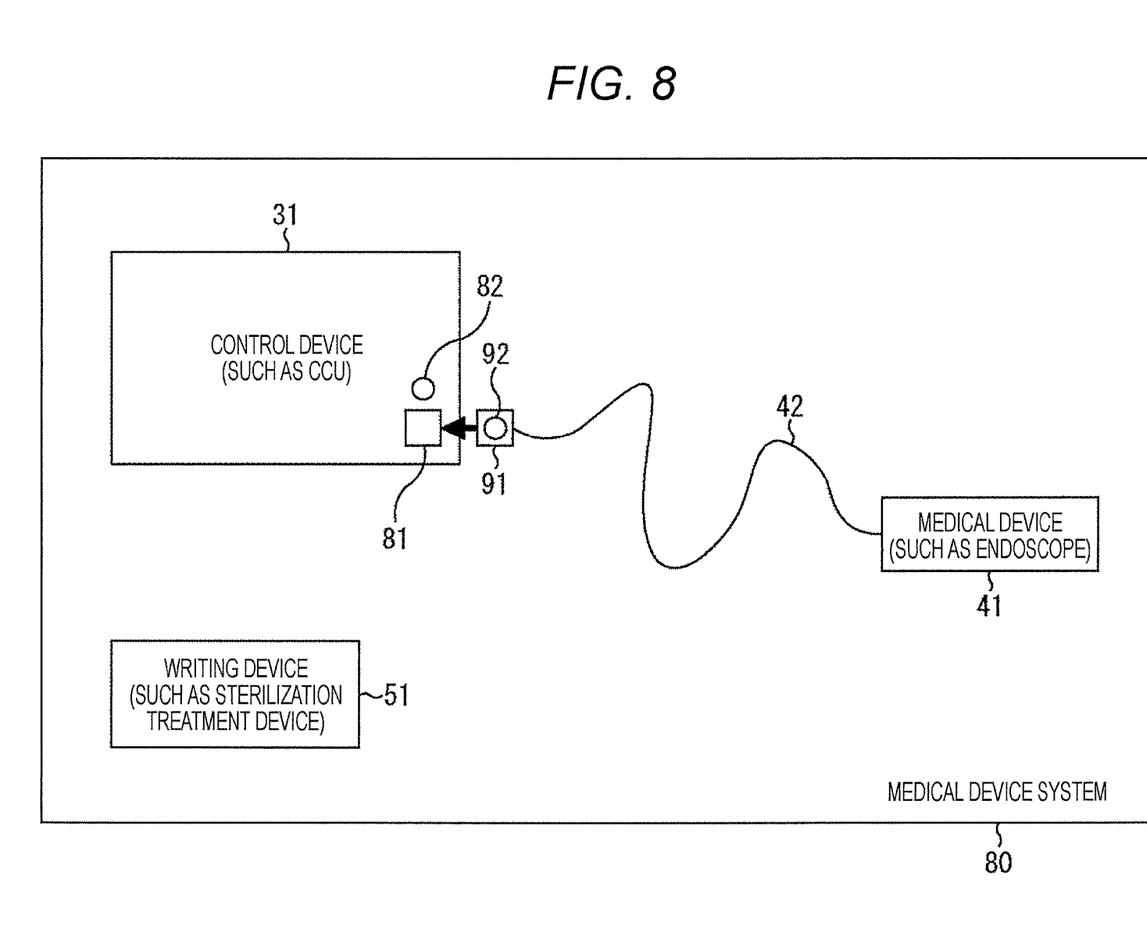
FIG. 8 is a block diagram illustrating another configuration example of the medical device system to which the present disclosure is applied.

FIG. 8 illustrates a configuration example of the medical device system to which the present disclosure is applied. A medical device system 80 allows a seal-shaped communication device capable of performing the radio communication by NFC to perform the above-described series of processes.

That is, a seal-shaped communication device 82 is affixed beside a connector insertion port 81 of the control device 31. The seal-shaped communication device 82 is obtained by omitting the writing unit 64 and the signal transmission unit 65 from the configuration example of the connector joint 32 illustrated in FIG. 3. However, as for the seal-shaped communication device 82, it is necessary to register the attribute information of the control device 31 to which this is affixed by a certain method.

A seal-shaped communication device 92 is affixed to a connector unit 91 provided at the end of the cable 42 extending from the medical device 41. The seal-shaped communication device 92 is obtained by omitting the sensor unit 74 and the signal transmission unit 75 from the configuration example of the connector unit 43 illustrated in FIG. 4. However, as for the seal-shaped communication device 92, it is necessary to register the attribute information of the medical device 41 to which this is affixed by a certain method.

By using the seal-shaped communication devices 82 and 92 as in the medical device system 80 illustrated in FIG. 8, it becomes possible to realize a function equivalent to that of the above-described medical device system 30 by so-called post-attachment.

<Example of Information Stored in Storage Unit 73 of Connector Unit 43>

Although the attribute information of the medical device 41, the information indicating whether the sterilization treatment is already performed and the like are stored in the storage unit 73 of the connector unit 43 in the description above, in addition to them, for example, the number of times of use and using time of the medical device 41, the number of times of connection to the control device 31, the fact that this breaks in a case where this breaks and the like may be stored. The information may be used for maintenance of the medical device 41, for example.

For example, in a case where the control device 31 corresponds to the light source device 6 in FIG. 1 and the medical device 41 corresponds to lighting of the endoscope 2, a type of the light source and the like may be stored. This information may be used, for example, for white balance (WB) processing on the moving image which is imaged.

In addition, for example, in a case where the control device 31 corresponds to the device for treatment tool 7 in FIG. 1 and the medical device 41 corresponds to the energy treatment tool 3, a voltage value, a resistance value and the like of a tip end of the energy treatment tool 3 (a portion which applies thermal treatment to the affected site) may be stored. This information may be used, for example, for maintenance of the energy treatment tool 3 and adjustment of an output of the high frequency current to be supplied.

Meanwhile, the embodiment of the present disclosure is not limited to the above-described embodiment, and various modifications may be made without departing from the gist of the present disclosure.

The present disclosure may also have the following configurations.

(1)

A control device including:

a connector joint to which a connector unit provided on a cable extending from a medical device is connected;

a communication unit that performs radio communication with the connector unit by proximity radio communication; and a notification unit that notifies a user of user support information based on information from the medical device received by the communication unit.

(2)

The control device according to (1) described above, in which the notification unit notifies the user whether the control device and the medical device are officially compatible with each other as the user support information.

(3)

The control device according to (1) or (2) described above, further including:

a compatibility determination unit that determines whether the control device and the medical device are officially compatible with each other on the basis of attribute information of the medical device received by the communication unit, in which the notification unit notifies the user of a determination result of the compatibility determination unit as the user support information.

(4)

The control device according to (3) described above, in which a determination criterion when the compatibility determination unit determines whether the control device and the medical device are officially compatible with each other on the basis of the attribute information of the medical device is able to be updated.

(5)

The control device according to any one of (1) to (4) described above, further including:

a connection determination unit that determines whether electrical connection between the control device and the medical device is stable, in which the notification unit further notifies the user of a determination result of the connection determination unit as the user support information in a state where the connector unit is connected to the connector joint.

(6)

The control device according to any one of (1) to (5) described above, in which the notification unit notifies the user whether an orientation of the connector unit matches the connector joint as the user support information in a state where the connector unit is not connected to the connector joint.

(7)

The control device according to any one of (1) to (6) described above, in which the notification unit notifies whether the medical device is already subjected to sterilization treatment as the user support information on the basis of the information from the medical device received by the communication unit.

(8)

The control device according to any one of (1) to (7) described above, in which the notification unit notifies of information regarding the number of times of use or using time of the medical device as the user support information on the basis of the information from the medical device received by the communication unit.

(9)
A medical device including:
a connector unit for connecting to a control device via a cable;
a communication unit that performs radio communication with the control device by proximity radio communication; and
a notification unit that notifies a user of user support information based on information from the control device received by the communication unit.

(10)
The medical device according to (9) described above,
in which the notification unit notifies the user whether the control device and the medical device are officially compatible with each other as the user support information.

(11)
The medical device according to (9) or (10) described above,
in which the communication unit transmits attribute information of the medical device to the control device and receives compatibility information indicating whether the control device and the medical device are officially compatible with each other transmitted from the control device, and
the notification unit notifies the user whether the control device and the medical device are officially compatible with each other as the user support information on the basis of the received compatibility information.

(12)
The medical device according to (9) or (10) described above, further including:
a compatibility determination unit that determines whether the control device and the medical device are officially compatible with each other on the basis of attribute information of the control device received by the communication unit,
in which the notification unit notifies the user of a determination result of the compatibility determination unit as the user support information.

(13)
The medical device according to any one of (9) to (12) described above, in which
a determination criterion when the compatibility determination unit determines whether the control device and the medical device are officially compatible with each other on the basis of the attribute information of the control device is able to be updated.

(14)
The medical device according to any one of (9) to (13) described above,
in which the notification unit further notifies the user whether electrical connection between the control device and the medical device is stable as the user support information in a state where the connector unit is connected to the control device.

(15)
The medical device according to any one of (9) to (14) described above,
in which the notification unit notifies the user whether an orientation of the connector unit matches a connector joint of the control device as the user support information in a state where the connector unit is not connected to the control device.

(16)
The medical device according to any one of (9) to (15) described above,
in which the notification unit notifies the user whether sterilization treatment of the medical device is already performed as the user support information.

(17)
The medical device according to any one of (9) to (16) described above,
in which the notification unit notifies the user of information regarding the number of times of use or using time of the medical device as the user support information.

(18)
A medical device system including: a control device; and a medical device connected to the control device via a cable,
in which the control device is provided with:
a connector joint connected to a connector unit of the medical device;
a first communication unit that performs radio communication with the connector unit of the medical device by proximity radio communication;
a first notification unit that notifies a user of user support information based on information from the medical device received by the communication unit; and
the connector unit of the medical device is provided with:
a second communication unit that performs radio communication with the first communication unit of the control device by proximity radio communication; and
a second notification unit that notifies the user of the user support information based on information from the control device received by the second communication unit.

REFERENCE SIGNS LIST

1 Endoscopic surgical system
2 Endoscope
3 Energy treatment tool
5 CCU
6 Light source device
7 Device for treatment tool
30 Medical device system
31 Control device
32 Connector joint
41 Medical device
42 Cable
43 Connector unit
61 Communication unit
64 Determination unit
65 Notification unit
64 Writing unit
65 Signal transmission unit
71 Communication unit
72 Notification unit
73 Storage unit
74 Sensor unit
75 Signal transmission unit
81 Connector insertion port
82 Seal-shaped communication device
91 Connector
92 Seal-shaped communication device

The invention claimed is:
1. A surgical system comprising:
circuitry configured to:
detect whether a first connection portion of a medical device is communicable with a second connection portion of a control device by wireless communication,
obtain information of the medical device when the first connection portion of the medical device connects the second connection portion of the control device, determine whether the control device and the medical device are compatible based on the information of the medical device and information of the control device, and notify a user of a connection method between the control device and the medical device when the control device and the medical device are compatible.

2. The surgical system according to claim 1, wherein the circuitry is further configured to determine whether the connection between the control device and the medical device is stable via the second connection portion by the wireless communication, and notify the user of the connection stability between the control device and the medical device.

3. The surgical system according to claim 2, wherein the circuitry is further configured to receive sterilization treatment information indicating whether the medical device is already subjected to sterilization treatment via the second connection portion by the wireless communication, and notify the user of the sterilization treatment information.

4. The surgical system according to claim 3, wherein the circuitry is further configured to notify the user of at least one of the connection stability, the sterilization treatment information, or the compatible information between the medical device and the control device by a light emitter.

5. The surgical system according to claim 4, wherein the circuitry is further configured to control the light emitter to change blinks and color depending on a type of information.

6. The surgical system according to claim 1, wherein the circuitry is further configured to receive usage information indicating a number of times of use or using time of the medical device via the second connection portion, notify the user of the usage information.

7. The surgical system according to claim 1, wherein the circuitry is further configured to stand by until a counterpart connectable to the second connection portion of the control device is within a communication range by the wireless communication.

8. The surgical system according to claim 1, wherein the circuitry is further configured to receive medical device information indicating a type of the medical device via the second connection portion by the wireless communication, and control the medical device based on the type of the medical device.

9. The surgical system according to claim 8, wherein the circuitry is further configured to receive the medical device information including a type of a light source device of an endoscope device via the second connection portion by the wireless communication, and control the endoscope device based on the type of the light source device.

10. The surgical system according to claim 9, wherein the circuitry is further configured to receive the medical device information including a characteristic value of an energy device via the second connection portion by the wireless communication, and control the energy device based on the characteristic value.

11. The surgical system according to claim 1, wherein the circuitry is further configured to notify the user of a physical connection method of the medical device and the control device when the control device and the medical device are compatible.

12. The surgical system according to claim 11, wherein the circuitry is further configured to notify the user of the physical connection method of the medical device and the control device when the control device and the medical device are compatible.

13. The surgical system according to claim 1, wherein the circuitry is further configured to start to communicate with the medical device when the first connection portion connectable to the second connection portion of the control device is within a communication range by the wireless communication.

14. The surgical system according to claim 1, wherein the medical device is an endoscope device.

15. A control device comprising:
circuitry configured to:
detect whether a first connection portion of a medical device is communicable with a second connection portion of the control device by wireless communication,
obtain information of the medical device when the first connection portion of the medical device connects the second connection portion of the control device,
determine whether the control device and the medical device are compatible based on the information of the medical device and information of the control device, and
notify a user of a connection method between the control device and the medical device when the control device and the medical device are compatible.

16. A method of a connection between a medical device and a control device in a surgical system by circuitry, comprising:
detecting whether a first connection portion of the medical device is communicable with a second connection portion of the control device by wireless communication;
obtaining information of the medical device when the first connection portion of the medical device connects the second connection portion of the control device;
determining whether the control device and the medical device are compatible based on the information of the medical device and information of the control device; and
notifying a user of the connection method between the control device and the medical device when the control device and the medical device are compatible.

* * * * *